United States Patent [19]

Rasmussen

[11] Patent Number: 4,524,775
[45] Date of Patent: Jun. 25, 1985

[54] MEDICAL ELECTRODE AND A METHOD OF MANUFACTURING SAME

[76] Inventor: Jan Rasmussen, Bøgevej 12, DK-3650 Ølstykke, Denmark

[21] Appl. No.: 466,164

[22] Filed: Feb. 14, 1983

[30] Foreign Application Priority Data

Feb. 15, 1982 [DK] Denmark .................. 647/82

[51] Int. Cl.³ .............................. A61B 5/04
[52] U.S. Cl. .................. 128/640; 128/641; 29/878; 29/882
[58] Field of Search ............... 128/639–641, 128/644, 798, 802, 803; 29/877, 878, 882

[56] References Cited

U.S. PATENT DOCUMENTS

| | | | |
|---|---|---|---|
| 3,828,766 | 8/1974 | Krasnow | 128/641 |
| 3,862,633 | 1/1975 | Allison et al. | 128/641 |
| 3,865,099 | 2/1975 | Robichaud | 128/641 |
| 3,964,469 | 6/1976 | Manley | 128/641 |
| 3,972,329 | 8/1976 | Kaufman | 128/641 |
| 3,977,392 | 8/1976 | Manley | 128/641 |
| 3,989,035 | 11/1976 | Zuehlsdorff | 128/641 |
| 4,019,500 | 4/1977 | Patrick, Jr. et al. | 128/641 |
| 4,040,412 | 8/1977 | Sato | 128/641 X |
| 4,114,263 | 9/1978 | Szpur | 128/641 X |
| 4,257,424 | 3/1981 | Cartmell | 128/641 |
| 4,350,165 | 9/1982 | Striese | 128/640 |
| 4,419,091 | 12/1983 | Behl et al. | 128/803 X |

FOREIGN PATENT DOCUMENTS 2552197  5/1976  Fed. Rep. of Germany ...... 128/641

Primary Examiner—Lee S. Cohen
Attorney, Agent, or Firm—Lewis H. Eslinger

[57] ABSTRACT

A medical electrode for contacting the skin comprises a foam plastic disc (10) which is formed with an aperture (11), and the part of the disc surrounding the aperture is covered by a cover foil (12) on one side thereof. A strip-shaped metal electrode (13) is placed below the foil in the aperture and is connected to the stripped end (14) of a plastic insulated lead (15), whose end portion is covered by the cover foil. The whole assembly is welded together to form a unit in that it is placed between two pressing plates which form a capacitor in a high-frequency circuit, and one of them is of the same size and shape as the cover foil and presses it a distance into the foam plastic disc, which is thus compressed in the area concerned and fixed in the compressed shape because the cell walls partly fuse. This increases the resistance of the foam plastics against diffusion of the components of the contact medium which in the use of the electrode is placed in the aperture (11), without any noticeable deterioration in the flexibility and pliability of the electrode.

10 Claims, 5 Drawing Figures

MEDICAL ELECTRODE AND A METHOD OF MANUFACTURING SAME

BACKGROUND OF THE INVENTION

The invention relates to a medical electrode comprising a foam plastic disc with an aperture to form a contact medium chamber and a foil, preferably of plastics, covering the aperture and at least a part of the foam plastic disc surrounding the aperture on one side of said disc, and a metal electrode disposed in the chamber and connected to a connector, a layer of an adhesive, preferably sensitive to pressure, being applied to the other side of the foam plastic disc.

Such electrodes are used for establishing electrical contact between the skin of humans or animals and electrical measuring equipment for measuring or detecting electrical signals or voltages produced in the skin areas in question as a result of physiological processes, such as the heart function. Plotting of curves indicative of this function is called electrocardiography, abbreviated as ECG, and electrodes of this type are therefore often called ECG electrodes.

As patients are often to be watched for long periods of time, e.g. several days, it is important that the electrodes add as little to the discomfort of the patient or carrier as possible. This is provided for to a great extent by the use of foam plastics, which is a soft and pliable material. It is also important that the paste-like contact medium, which is generally used for establishing good electrical connection between the metal electrode and the skin, can be kept intact during the entire period of operation. This means that the walls defining the contact medium chamber must be so tight as to allow no considerable diffusion of the constituent components of the contact medium.

The U.S. Patent Specification No. 3,977,392 discloses a medical electrode of the present type in which the contact medium is in direct contact with the foam plastic walls defining the aperture for receiving the medium, and though foam plastics with closed cells is used it has been found that diffusion nevertheless takes place through them, leading to deterioration of the properties of the contact medium and increased contact resistance.

The U.S. Patent Specifications No. 4,019,500 and 4,114,263 disclose medical electrodes in which diffusion of contact medium components is prevented by the use of a plastic cup which is attached to the foam plastic disc and forms the contact medium chamber. However, such plastic cups make the electrodes relatively rigid and thus add to patient discomfort.

SUMMARY OF THE INVENTION

The object of the invention is to provide a medical electrode of the present type which combines a high degree of patient comfort with a capacity of maintaining good contact properties over extended periods of use.

This object is achieved in that the foam plastics in an area around and adjoining the chamber is compressed, and that the cell walls in said area are partly fused. As the parts of the foam plastic disc adjoining the contact medium chamber are compressed and the plastic cell walls are partly fused, the foam plastics becomes so tight that practically no diffusion can take place through it, without the compression and fusing noticeably increasing the rigidity of the electrode. Thus, a medical electrode is provided which is permeable to sweat in the adhering zone, but forms a barrier to moisture in the measuring area. The preferred foam plastics is PVC foam.

The U.S. Patent Specification No. 4,257,424 discloses a medical electrode where the foam plastic disc has been compacted to some extent around the aperture by the insertion into said aperture of a sponge whose diameter is greater than the diameter of the aperture so that its edge portion is pressed together by the foam plastic disc, which thus itself is pressed somewhat together. However, the cell walls of the disc have not been fused.

The invention also concerns a method of manufacturing the medical electrode, and when the foam plastic disc and the foil are heated in engagement with each other between two pressing means, one of which having substantially the same shape and extent as the foil, both the compression and the fusion can be effected in one and the same operation.

When a foil-like metal electrode extending into the chamber and a plastic insulated lead with a stripped end portion welded to the metal electrode are interposed between the foam plastic disc and the foil, and the heating is effected to such a temperature as will make the lead insulation fuse together with the foil and the foam plastics, external influences on the wire connecting the metal electrode to external electrical equipment will not be transferred to the metal electrode to a substantial extent and cause it to be moved, which might lead to variations in the contact resistance and thus unreliable measuring results. This favourable effect is due to the tensile relief of the metal electrode produced by the fusion of the wire insulation with the foil and the foam plastics. The circumstance that this fusion is effected in the same operation as the abovementioned compression and cell wall fusion greatly contributes to making the entire manufacturing process simpler and cheaper.

An expedient method of manufacturing a medical electrode with a connector in the form of a snap lock is one wherein a foil-like metal electrode extending into the chamber is interposed between the foam plastic disc and the foil, and a portion of the foil together with an end portion of the metal electrode is clamped between two flanges on a lower part and an upper part, respectively, of a two-part connector in the form of a snap lock means.

More particularly, the lower part of the snap lock means is so mounted in a aperture in the cover foil that its flange is completely covered by foil, which along and outside the periphery of the flange is welded to a second piece of cover foil placed on the underside of the lower part.

Also the latter two embodiments provide for tension relief of the metal electrode in the connector.

In practice the various fusing and welding operations preferably take place by heating, which is effected by passing high-frequency current to the two pressing means acting as capacitor plates.

DESCRIPTION OF THE DRAWINGS

The invention will be explained more fully below with reference to the drawing, in which.

DESCRIPTION OF THE PREFERRED EMBODIMENT

Figure 1:
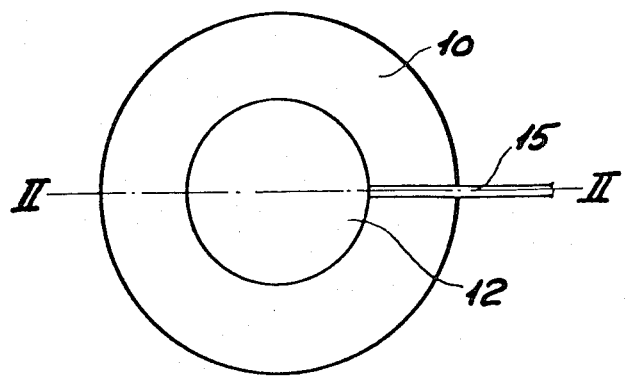
FIG. 1 is a top view of an embodiment of the medical electrode of the invention.
Figure 2:
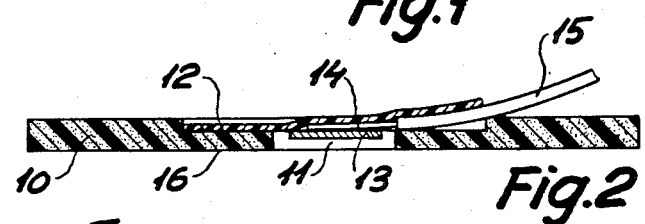
FIG. 2 is a section taken along the line II—II in FIG. 1, FIGS. 3 and 4 are top and bottom views, respectively, of another embodiment of the medical electrode of the invention.

The medical electrode shown in FIGS. 1 and 2 has a circular disc 10 of foam plastics, e.g. foamed PVC, with a central aperture forming a chamber 11 for receiving a contact medium (not shown), which is generally a paste-like electrolyte. A piece of plastic foil 12 is placed at one side of and concentrically with the foam plastic disc and is pressed down into the soft foam plastics and defines the chamber 11 at one side. The underside of the plastic foil 12 has attached to it a metal electrode 13, preferably in the form of a strip of silver foil on whose upper side the stripped end 14 of a plastic insulated lead 15 is welded. As appears from the drawing not only the stripped conductor section 14 but also an end portion of the lead insulation is covered by the plastic foil 12. The end of the lead 15 which is not shown may be conveniently applied to a suitable connector (not shown), e.g. a banana plug socket. A layer of pressure-sensitive glue 16, which does not hurt the skin, is applied to the underside of the foam plastic disc 10 to retain the electrode on the skin.

The shown medical electrode is manufactured by placing the various parts in their proper mutual positions between a flat metal substrate and a metal pressing plate of the same shape and size as the plastic foil piece 12, and the pressing plate is moved so far down towards the substrate that the part of the foam plastic disc 10 aligned with the plastic foil is compressed as shown in FIG. 2. The substrate and the pressing plate form a capacitor inserted in a high-frequency circuit (not shown), and heat is developed between these plates as a consequence of dielectric losses. The heat causes the walls of the compressed foam plastic cells to fuse partly so that the part of the foam plastic disc in question is fixed in the compressed shape and becomes so tight as to allow no diffusion of the constituent components of a contact paste placed in the chamber 11. At the same time the plastic foil 12 is welded to the foam plastic disc and the insulation of the lead 15, which in turn is welded to the foam plastic disc to provide effective tension relief of the metal electrode 15, which has been prewelded to the end 14 of the lead.

Figure 3:
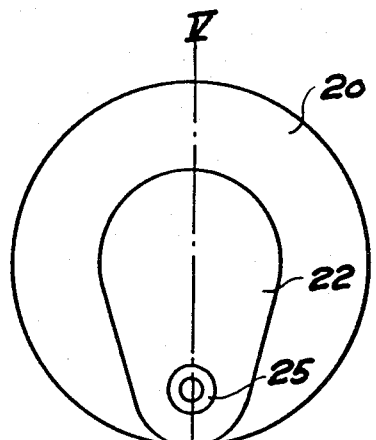
Figure 4:
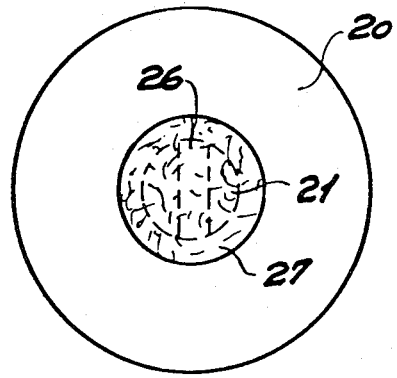
Figure 5:
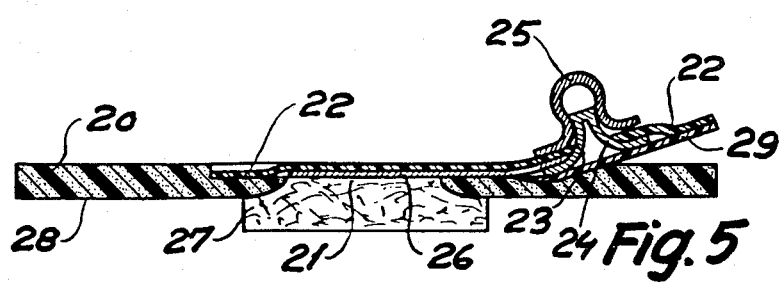
FIG. 5 is a section taken along the line V—V in FIG. 3.

FIGS. 3-5 show a medical electrode having a connector in the form of a snap lock. This electrode, like the one shown in FIGS. 1 and 2, has a foam plastic disc 20 with a central aperture 21, a piece of cover foil 22, which here not only covers an area of the disc 20 surrounding the aperture 21, but has a radial portion extending to the periphery of the disc. Adjacent its outer end the cover foil 22 has an opening 23 in which a snap lock lower part 24 is fitted; the lower part 24 has a flange on whose underside is placed a second piece of cover foil 29, which is welded to the first cover foil 22 along the edge. A similar flange on the upper part 25 of the snap lock engages the upper side of the cover foil 22, which is thus sandwiched between the two snap lock parts. A metal electrode in the form of a silver-silverchloride strip 26 extends across the aperture 21 between the foam plastic disc and the cover foil and across part of the flange of the snap lock lower part 24.

The compression of the part of the foam plastic disc 20 surrounding the aperture 21 causes said aperture to become so shallow that the necessary electrical contact between the electrode strip 26 and the skin can be established by means of a sponge 27, in which a contact medium has been absorbed and which is adhered to the foam plastics around the aperture 21 by means of the glue film 28 on the underside of the electrode.

The details of the shown and described structure can be modified in many ways. For example, the snap lock in the embodiments of FIGS. 3-5 might be disposed in the centre of the electrode or completely outside of the foam plastic disc, and also other forms of connectors might be used. Further, other materials than those mentioned in the foregoing may be used. Moreover, the heat required for carrying out the various welding processes may be generated in other ways than by high-frequency currents, e.g. by means of ultrasound or by heating of the pressing means.

What is claimed is:

1. A medical electrode comprising:
    a foamed plastic disc having first and second sides with an aperture extending therebetween and forming a contact medium chamber, said foamed plastic disc comprising a plurality of cells with walls, said walls of said cells surrounding and adjoining said chamber being compressed and at least partially fused;
    a plastic foil cover covering said aperture and at least a part of said foamed plastic disc surrounding said aperture on one of said sides of said disc;
    connector means adapted to be electrically connected to monitoring equipment;
    a metal electrode disposed in said chamber and electrically connected to said connector means; and
    a layer of pressure-sensitive adhesive applied to the other of said sides of said disc.

2. The electrode of claim 1; wherein said foamed plastic disc is foamed polyvinylchloride.

3. The electrode of claim 1; wherein said metal electrode is of a foil material; and said connector means includes a plastic insulated lead having a stripped end portion welded to said metal electrode, said foil metal electrode and said plastic insulated lead being interposed between said foamed plastic disc and said foil cover, and the insulation of said plastic insulated lead being fused with said foil cover and said foamed plastic.

4. The electrode of claim 1; wherein said metal electrode is a foil material; and said connector means is a two-part connector with upper and lower portions with a flange on each of said upper and lower portions; and wherein a portion of said foil cover and an end portion of said foil metal electrode are clamped between said flanges.

5. The electrode of claim 4; wherein said foil cover has an aperture therein; and wherein said lower portion of said two-part connector is mounted in said aperture in said foil cover so that said foil cover completely covers said flange on said lower portion; and further comprising a second foil cover in addition to the firstmentioned foil cover positioned on an underside of said lower portion of said two-part connector, said second foil cover having an edge welded to said first foil cover.

6. A method of manufacturing a medical electrode comprising the steps of:
    providing a foamed plastic disc having first and second sides with an aperture extending therebetween and defining a contact medium chamber;

providing a plastic foil cover in contact with said disc for covering said aperture of said disc and at least a portion of one side of said disc surrounding said aperture;

positioning said disc and said plastic foil cover in contact therewith between at least two pressing means, with one of said pressing means having substantially the same shape as said foil cover;

compressing said foamed plastic adjacent and surrounding said aperture;

heating said disc and said foil cover to fuse at least part of said foamed plastic surrounding said aperture;

disposing a foil metal electrode between said foamed plastic disc and said plastic foil cover, said foil metal electrode extending into said chamber; and applying a layer of pressure-sensitive adhesive to the other of said sides of said disc.

7. The method of claim 6; wherein said foil metal electrode has a lead extending between said plastic foil cover and said foamed plastic disc, with plastic insulation and a stripped end portion welded to said electrode; and wherein said step of heating said disc and said plastic foil cover includes heating said insulation to fuse said insulation with said foil cover and said foamed plastic.

8. The method of claim 6; further comprising the steps of providing a two-part connector as a snap-lock means; and clamping a portion of said plastic foil cover together with an end portion of said foil metal electrode between two flanges on a lower portion and an upper portion, respectively, of said two-part connector.

9. The method of claim 8; and further comprising the steps of mounting said lower portion of said two-part connector in an aperture in said foil cover so that one of said flanges is completely covered therewith; providing a second foil cover in addition to the first-mentioned foil cover positioned on an underside of said lower portion of said two-part connector; and welding an edge of said second foil cover to said first foil cover.

10. The method of claim 9; wherein the step of heating said disc and said foil cover includes the step of supplying a high-frequency current to said two pressing means whereby said pressing means function as capacitor plates.

* * * * *